United States Patent
Enderle et al.

(10) Patent No.: US 11,052,257 B2
(45) Date of Patent: Jul. 6, 2021

(54) METHOD AND DEVICE FOR QUANTIFICATION OF NEUROMUSCULAR STIMULATIONS DUE TO RF-CURRENTS

(71) Applicant: Erbe Elektromedizin GmbH, Tuebingen (DE)

(72) Inventors: Markus Enderle, Tuebingen (DE); Ulrich Biber, Reutlingen (DE); Ovidiu Jurjut, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 0 days.

(21) Appl. No.: 16/883,489

(22) Filed: May 26, 2020

(65) Prior Publication Data
US 2020/0376283 A1     Dec. 3, 2020

(30) Foreign Application Priority Data
May 27, 2019 (EP) .................................. 19176733

(51) Int. Cl.
| | |
|---|---|
| A61N 1/00 | (2006.01) |
| A61N 1/372 | (2006.01) |
| A61N 1/02 | (2006.01) |
| A61N 1/04 | (2006.01) |
| A61N 1/36 | (2006.01) |
| A61N 1/378 | (2006.01) |

(52) U.S. Cl.
CPC ......... *A61N 1/37241* (2013.01); *A61N 1/025* (2013.01); *A61N 1/0452* (2013.01); *A61N 1/36007* (2013.01); *A61N 1/36192* (2013.01); *A61N 1/3787* (2013.01)

(58) Field of Classification Search
CPC ............ A61N 1/37241; A61N 1/36007; A61N 1/3787; A61N 1/0452; A61N 1/36192; A61N 1/025
See application file for complete search history.

(56) References Cited

FOREIGN PATENT DOCUMENTS

WO    2004/016315 A1    2/2004

OTHER PUBLICATIONS

Extended European Search Report dated Nov. 20, 2019, in corresponding European Application No. 19176733.4, with machine English translation (13 pages).
(Continued)

*Primary Examiner* — Mallika D Fairchild
(74) *Attorney, Agent, or Firm* — Fitch, Even, Tabin & Flannery LLP

(57) ABSTRACT

A two-part NMS-test bench is provided with which instruments, generator voltages, and surgery modes can be evaluated with regard to neuromuscular stimulations. By separating the NMS-test bench in a first part for application of the instrument and in the second part for evaluation of the physiological effect on nerves, a measurement free of artifacts is possible. The spatial and timely separation of the RF-application from the recording of the compound action potentials makes RF-disturbances ineffective. The electrical signals gained in the instrument test chamber can be preprocessed. The recorded electrical signals emitted from the instrument can be evaluated at the nerve model an arbitrary number of times. The variance involved with the recording of compound action potentials during direct use of the instrument can thus be minimized. The separated test of the signals at the nerve model avoids thermal damage of a prepared nerve and falsification of measurement results.

15 Claims, 1 Drawing Sheet

(56) References Cited

OTHER PUBLICATIONS

"PRO Lesson A03—Compound Action Potential: Nerve Conduction Using the frog sciatic nerve," Bioopac Systems, Inc., Oct. 23, 2015, pp. 1-22 (22 pages).
Lei Chen et al., "Experiment on building a real-time temperature field distribution model of the prostate using special data encryption multi-pole radiofrequency ablation and a visualization phantom," Chinese Science Bulletin, Dec. 3, 2011, pp. 3845-3853, vol. 56, No. 35 (10 pages).
Stavros G. Demos et al., "Real time assessment of RF cardiac tissue ablation with optical spectroscopy," Optics Express, Sep. 12, 2008, pp. 15286-15296, vol. 16, No. 19 (11 pages).
Kutan Ozer et al., "Bladder injury secondary to obturator reflex is more common with plasmakinetic transurethral resection than monopolar transurethral resection of bladder cancer," Central European Journal of Urology, Sep. 26, 2015, pp. 284-288, vol. 68 (5 pages).
J. Ferlay et al., "Estimates of the cancer incidence and mortality in Europe in 2006," Annals of Oncology, Feb. 7, 2007, pp. 581-592, vol. 18, No. 3 (12 pages).
Ingo Kausch et al., "Recent improvements in the detection and treatment of nonmuscle-invasive bladder cancer," Expert Rev. Anticancer Ther., 2006, pp. 1301-1311, vol. 6, Issue 9 (11 pages).
Carol E. Desantis et al., "Cancer Treatment and Survivorship Statistics, 2014," CA: A Cancer Journal for Clinicians, 2014, pp. 252-271, vol. 64, No. 4 (20 pages).
Mee Kristine AAS-ENG et al., "Complications in operative hysteroscopy—is prevention possible?," Acta Obstetricia et Gynecologica Scandinavica, Aug. 18, 2017, pp. 1399-1403, vol. 96, Issue 12 (5 pages).
Mark S. Shulman et al., "Simultaneous Bilateral Obturator Nerve Stimulation During Transurethral Electrovaporization of the Prostate," Journal of Clinical Anesthesia, Sep. 1998, pp. 518-521, vol. 10, Issue 6 (4 pages).
Florella Magora et al., "Obturator Nerve Block: An Evaluation of Technique," British Journal of Anaesthesia, Aug. 1969, pp. 695-698, vol. 41, Issue 8 (4 pages).
Peter G. Atanassoff et al., "Electromyographic Comparison of Obturator Nerve Block to Three-in-One Block," Anesth Analg, Sep. 1995, pp. 529-533, vol. 81, Issue 3 (5 pages).
Peter G. Atanassoff et al., "Compound Motor Action Potential Recording Distinguishes Differential Onset of Motor Block of the Obturator Nerve in Response to Etidocaine or Bupivacaine," Anesth Analg, Feb. 1996, pp. 317-320, vol. 82, Issue 2 (4 pages).
Deniz Bolat et al., "Impact of nerve stimulator-guided obturator nerve block on the short-term outcomes and complications of transurethral resection of bladder tumour: A prospective randomized controlled study," Canadian Urological Association, Nov.-Dec. 2015, pp. E780-E784, vol. 9, Issues 11-12 (5 pages).
Mohammadhatef Khorrami et al., "A Comparison Between Blind and Nerve Stimulation Guided Obturator Nerve Block in Transurethral Resection of Bladder Tumor," Journal of Endourology, Oct. 2012, pp. 1319-1322, vol. 26, No. 10 (5 pages).
W. Wieland et al., "Transurethrale Resektion der Blase," Endoskopische Urologie, 2009, pp. 124-134, with machine English translation (13 pages).
Narmada P. Gupta et al., "Bipolar energy for transurethral resection of bladder tumours at low-power settings: initial experience," BJU International, Dec. 22, 2010, pp. 553-556, vol. 108, Issue 4 (4 pages).
J. Biserte et al., "Traitement des tumeurs superkielles de vessie par laser Argon," Acta Urologica Belgica, 1989, pp. 697-701, vol. 57, No. 3, with English translation of the Abstract (5 pages).
Michael Alschibaja et al., "Recent improvements in transurethral high-frequency electrosurgery of the prostate," BJU International, Jan. 17, 2006, pp. 243-246, vol. 97, Issue 2 (4 pages).

Hiroaki Shiozawa et al., "A New Transurethral Resection System: Operating in Saline Environment Precludes Obturator Nerve Reflexes," The Journal of Urology, Dec. 1, 2002, pp. 2665-2667, vol. 168, Issue 6 (3 pages).
3unnar Wendt-Nordahl et al., "The Vista System: A New Bipolar Resection Device for Endourological Procedures: Comparison with Conventional Resectoscope," European Urology, Nov. 2004, pp. 586-590, vol. 46, Issue 5 (5 pages).
Chenming Zhao et al., "Bipolar Versus Monopolar Transurethral Resection of Nonmuscle-Invasive Bladder Cancer: A Meta-Analysis," Journal of Endourology, Jan. 11, 2016, pp. 5-12, vol. 30, No. 1 (8 pages).
V. Venkatramani et al., "Monopolar versus Bipolar Transurethral Resection of Bladder Tumors: A Single Center, Parallel Arm, Randomized, Controlled Trial," The Journal of Urology, Jun. 2014, pp. 1703-1707, vol. 191, Issue 6 (2 pages).
Toru Sugihara et al., "Comparison of Perioperative Outcomes including Severe Bladder Injury between Monopolar and Bipolar Transurethral Resection of Bladder Tumors: A Population Based Comparison," The Journal of Urology, Nov. 2014, pp. 1355-1359, vol. 192, Issue 5 (5 pages).
Joseph Mashni et al., "Prospective evaluation of plasma kinetic bipolar resection of bladder cancer: comparison to monopolar resection and pathologic findings," International Urology and Nephrology, Sep. 2014, pp. 1699-1705, vol. 46(9) (18 pages).
Marko Babjuk et al., "EAU Guidelines on Non-Muscle-invasive Urothelial Carcinoma of the Bladder: Update 2016," European Urology, Mar. 2017, pp. 447-461, vol. 71, Issue 3 (15 pages).
The New York School of Regional Anesthesia, ed. Obturator Nerve Block, 2018, accessed Feb. 26, 2018 on https://www.nysora.com/obturator-nerve-block (12 pages).
Peter G. Atanassoff et al., "Lidocaine Plasma Levels Following Two Techniques of Obturator Nerve Block," Journal of Clinical Anesthesia, Nov. 1996, pp. 535-539, vol. 8, Issue 7 (5 pages).
Manabu Kakinohana et al., "Interadductor approach to obturator nerve block for transurethral resection procedure: comparison with traditional approach," Journal of Anesthesia, May 2002, pp. 123-126, vol. 16 (4 pages).
Ch. Deliveliotis et al., "The contribution of the obturator nerve block in the transurethral resection of bladder tumors," Acta Urologica Belgica, Aug. 31, 1995, pp. 51-54, vol. 63(3) (4 pages).
R. Schwilick et al., "Die Ausschaltung des Obturatorius-Reflexes als spezifische Indikation für verdünnte Etidocain-Lösungen: Eine Untersuchung zur Eignung des Lokalanaesthetikums für die Reflex-Elimination in der Technik des '3-in-1 Blocks'," Regional-Anaesthesie, 1990, pp. 6-10, vol. 13, with English translation of the Abstract (5 pages).
James P. Gasparich et al., "Use of Nerve Stimulator for Simple and Accurate Obturator Nerve Block Before Transurethral Resection," The Journal of Urology, Aug. 1, 1984, pp. 291-293, vol. 132 (3 pages).
Yu Cui et al., "Comparing the Efficiency and Safety of Bipolar and Monopolar Transurethral Resection for Non-Muscle Invasive Bladder Tumors: A Systematic Review and Meta-Analysis," Journal of Laparoendoscopic & Advanced Surgical Techniques, Mar. 18, 2016, pp. 196-202, vol. 26, No. 3 (7 pages).
Ulrich Biber et al., "Turb Model—Voltage Recording at Obturator Nerve Site," Erbe Test Report, Jan. 11, 2018, pp. 1-33 (33 pages).
John R. Lacourse et al., "Effect of High-Frequency Current on Nerve and Muscle Tissue," IEEE Transactions on Biomedical Engineering, Jan. 1985, pp. 82-86, vol. BME-32, No. 1 (5 pages).
Louis Lapicque, "Techerches quantitatives sur l'excitation électrique des nerfs traitée comme une polarisation," J. Physiol Pathol Gen, 1907, pp. 620-635, with machine English translation (31 pages).
Ulrich Biber, "Nerve Model—Response to Turb Voltage Recordings from Different Electrosurgical Systems," Erbe Test Report, Feb. 14, 2019, pp. 1-39 (39 pages).

METHOD AND DEVICE FOR QUANTIFICATION OF NEUROMUSCULAR STIMULATIONS DUE TO RF-CURRENTS

RELATED APPLICATION(S)

This application claims the benefit of European Patent Application No. 19176733.4, filed May 27, 2019, the contents of which are incorporated herein by reference as if fully rewritten herein.

TECHNICAL FIELD

The invention refers to a method for quantification of neuromuscular stimulations external of a living organism as well as a device for carrying out this method.

BACKGROUND

It is known that neuromuscular stimulations can originate from electrosurgical instruments. Indeed electrosurgical instruments are typically applied with a radio frequency voltage, the frequency of which is above the stimulation threshold for nerves, however, neuromuscular stimulations cannot be reliably excluded. Amongst others such neuromuscular stimulations can occur during the transurethral electro-resection of the urinary bladder as well as during the transurethral electro-resection of the bladder or the prostate in the urology or during the hysteroscopic transcervical resection in gynecology. For example, potential intraoperative complications can occur, amongst others hemorrhages or even bladder perforations during a resection of a tumor of urinary tracts. Typically this is the consequence of a stimulation of the obturator nerve along with a sudden and vehement leg adductors contraction. Such a bladder wall perforation is in any case an incident to be avoided. Known possibilities for avoidance consist of the pharmacological blocking the ability to stimulate the obturator nerve, a deep relaxation of the skeletal muscles of the patient or the operation of the instrument with very low energy input. Each of these measures is correlated with specific disadvantages such that they cannot be recommended as general remedy for avoidance of neuromuscular stimulations. Thus, influence parameters of neuromuscular stimulations shall be investigated in order to consider these during a conception of instruments, generators and surgery regulations.

For this it is the object of the invention to provide a reproducible determination of neuromuscular stimulations in selected instruments, surgery methods, generator adjustments and surgery techniques.

SUMMARY

This object is solved with a method and a test device as described herein.

The inventive method using an instrument test chamber for reproducible testing of an instrument and for recording of electric signals that can be detected in the instrument test chamber when the instrument is activated. The method further uses a nerve test chamber in which signals for stimulation of a nerve model that have been gained by means of the instrument test chamber and that are potentially standardized with reference to their amplitude and/or filtered with reference to their frequency content or otherwise processed and in which the compound action potentials derived therefrom can be measured. The nerve model can be a mathematical model, a model realized by a computer program, a digital or analog model realized by hardware or a prepared nerve. The invention allows the quantification of neuromuscular reactions during use of electrosurgical systems. Such an electrosurgical system is considered to be the entirety consisting of the instrument provided for surgery, the desired voltage form of the RF-voltage and RF-power supplied from the generator to the instrument, as well as the type of the electrosurgical use, e.g. the incision. Due to the inventive method for quantification of neuromuscular stimulations external from a living organism, the risk of neuromuscular stimulations by an electrosurgical system can be quantified already prior to the use with animals or human beings. Thus, a platform is provided that basically adjusts the risk of neuromuscular stimulations in a new electrosurgical system on a clinically acceptable level without the need to execute animal experiments. This allows the acceleration of the development of electrosurgical instruments with concurrently improved safety.

The invention is based on the separation of the evaluation of the electrosurgical system from the evaluation of the effect on a prepared nerve or a nerve model. The instrument test chamber is part of the evaluation of the electrosurgical system in which the instrument is located that has to be evaluated and is applied with an RF-voltage of a predefined curve characteristic (wave form) and is positioned in a predefined manner. The positioning of the instrument can comprise the arrangement thereof at a predefined location in the instrument test chamber. The positioning can also comprise the movement of the activated instrument, i.e. the instrument to which the RF-voltage is applied, along a predefined path.

In the instrument test chamber at least one electrical signal is recorded from which a stimulation signal is determined. The stimulation signal is provided to the nerve model that is stimulated with the stimulation signal in this way and can accordingly output compound action potentials. The latter are detected and used for evaluation of the neuromuscular stimulation. For this it can be, e.g. stored in a database together with the other test conditions (instrument type, RF-voltage form, stimulation voltage or power, surgery paths).

The nerve model can be a technical model (electrical analog or digital circuit or computer program), as already mentioned. Alternatively, the nerve model can be formed by a nerve test chamber that comprises at least a stimulation electrode pair and at least a diverting electrode pair, wherein prepared functional nerve is placed in the nerve test chamber such that it is in contact with the stimulation electrode pair as well as the diverting electrode pair in order to measure the compound action potentials. The electrical signal recorded in the instrument test chamber can be first stored or also directly processed for determination of the stimulation signal. If necessary, additionally or alternatively the determined stimulation signal can be stored. The processing of the electrical signal for determination of the stimulation signal can comprise a filtering, particularly a low pass filtering and/or a temporal scaling and/or an amplitude scaling. The stimulation signal can be standardized for amplitude scaling in that it is referenced with a reference stimulation voltage. For this a standard signal, e.g. a square wave pulse with 7 V stimulation amplitude and a duration of 100 µs can be supplied to the nerve model as stimulation signal and therefrom the compound action potential with maximum response amplitude can be determined. In a next step the stimulation potential can be determined that is sufficient to obtain a compound action potential that can only just be measured. In doing so, the responsivity of the nerve can be checked based on empirical limit values. In a further step the stimulation signal obtained during the experiment by use of a real instrument in the measuring chamber can be amplified or attenuated until it corresponds to the compound action potential gained by the test impulse or with a defined fraction thereof. In doing so, the stimulation signal is preferably adjusted to an amplitude that yields to a compound action potential that is smaller than the maximum compound action potential, however, larger than the minimum compound action potential that can be measured at a nerve model. The inventive method can also comprise that the compound action potential provided by the nerve model is further processed before it is used for the evaluation of a surgical system. For this a non-functional nerve that can be for example removed from an animal, can be arranged in the nerve test chamber that is applied with the same stimulation signal as the functional nerve. The signal provided by the non-functional nerve can be subtracted from the compound action potential of the functional nerve in order to calculate a signal transmission of the stimulation signal from the compound action potentials that does not stem from the function of the nerve.

The non-functional nerve can be a prepared nerve with a bruise location that is placed between the stimulation electrode pair and the diverting electrode pair.

The device for quantification of neuromuscular stimulations external from a living organism that also belongs to the invention is suitable and configured for carrying out the inventive method. For this the device comprises particularly an instrument test chamber comprising a first compartment and a second compartment that are separated from each other by a wall and that are at least partly filled with the same or different liquids respectively. The liquid is preferably an electrolyte, preferably saline solution at least in one of the compartments, preferably in the second. While the instrument is arranged in the first compartment and is potentially moved, the diverting electrodes are positioned in the second compartment. The wall for separation of the compartments can be formed by tissue explanted from an organism, e.g. a bladder wall. It is, however, also possible to configure the wall from another natural material or plastic material in order to provide reproducible results.

A processing unit is also part of the device to which the signals output from the diverting electrodes are supplied. These signals can be directly supplied from the diverting electrodes to the processing unit or can be buffered before. In the latter case a storage device is arranged between the diverting electrodes and the processing unit.

The processing unit can serve for scaling, standardizing and/or filtering of the electrical signals delivered from the diverting electrodes in order to form stimulation signals for the nerve model therefrom.

With the presented methods and the presented device it is possible to test surgery systems under reproducible conditions and to examine the effect of modifications with reference to instrument configuration and/or RF-voltage form and/or energy input and/or movement of the instrument. In doing so, it is possible to contrast different surgery systems and compare them, for example, with regard to the used instruments and their electrode shapes, the used RF-voltage and the wave form thereof as well as with reference to the incision path.

BRIEF DESCRIPTION OF THE DRAWINGS

The drawings show a device for quantification of neuromuscular stimulations external from a living organism. They show.

DETAILED DESCRIPTION

Figure 1:
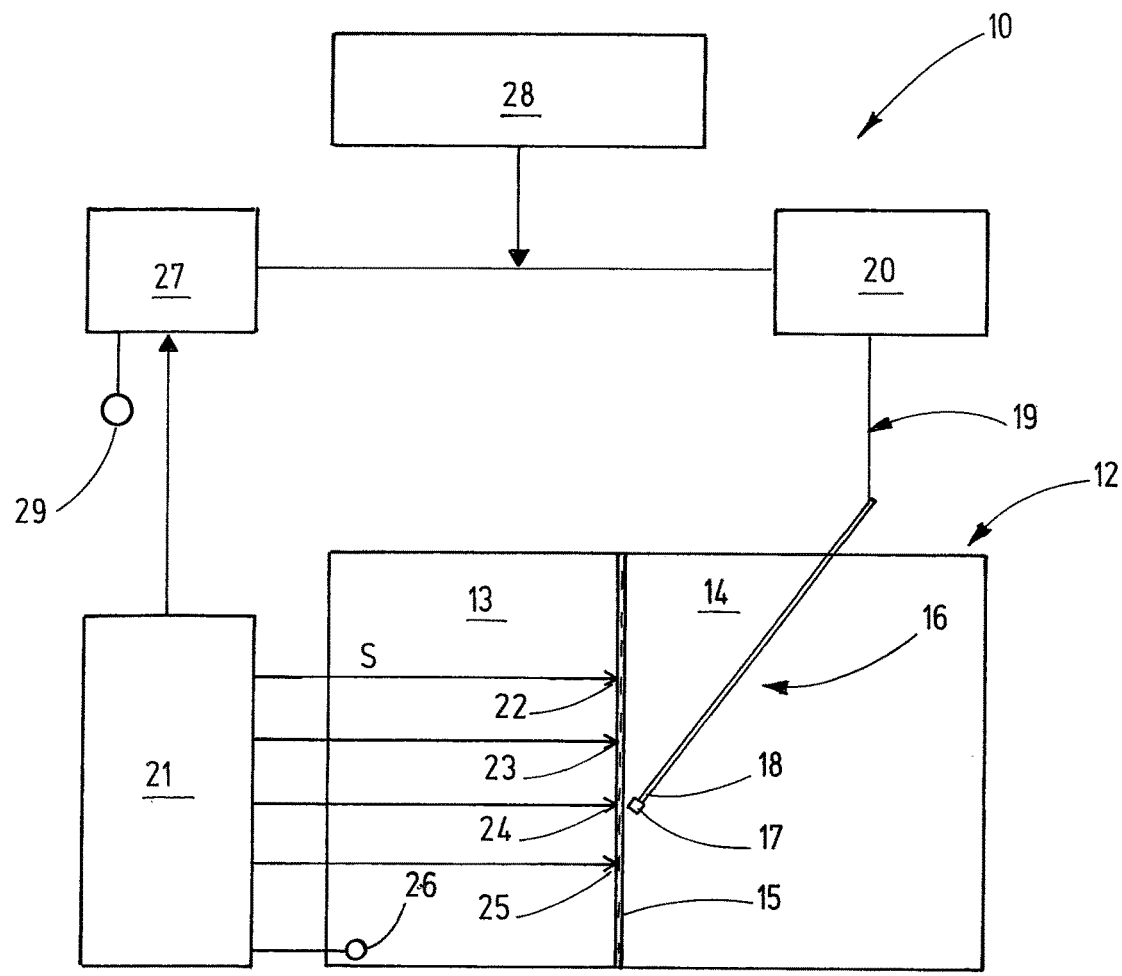
FIG. 1 an instrument test chamber with associated components.
Figure 2:
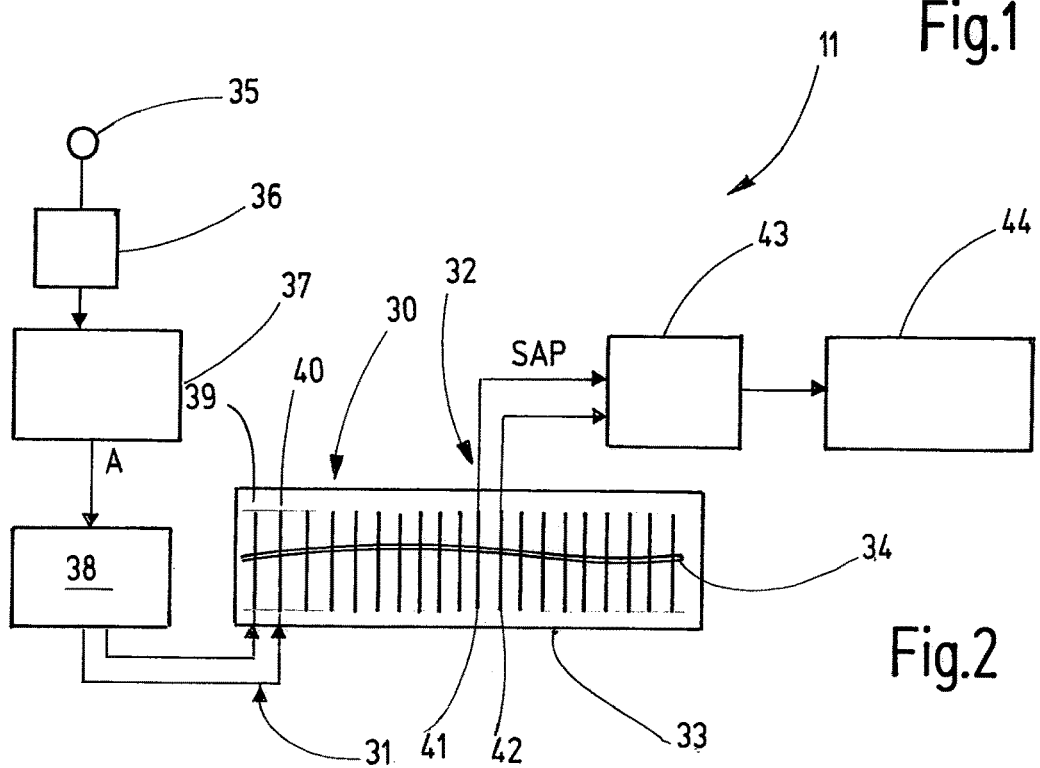
FIG. 2 a nerve model with associated components, in basic illustrations respectively.

FIG. 1 shows a part of a device 10 for quantification of neuromuscular stimulations external from a living organism that is subsequently referenced as NMS-test bench. A second part 11 of the NMS-test bench is illustrated in FIG. 2.

An instrument test chamber 12 is part of the NMS-test bench 10 according to FIG. 1 that comprises two compartments 13, 14 that are separated from each other by a wall 15, preferably a semi-permeable wall 15. The wall 15 can consist particularly from an explanted biological material, such as e.g. a pig bladder or another biological tissue. Alternatively, the wall 15 can also be made from a fine porous plastic material, a felt or the like, as long as it is guaranteed that the electrical voltage transmission between the two compartments 13, 14 is equal or similar to the voltage transmission of a pig bladder or another biological material to be examined.

Both compartments 13, 14 are filled with liquid. A compartment 13 is preferably filled with an electrolyte, particularly saline solution, e.g. a physiological saline solution. The compartment 14 is filled with a fluid that shall be used during a real surgery, e.g. also a physiological saline solution or also another electrolytic conducting or non-conducting fluid.

In the compartment 14 a surgical instrument 16 is arranged that is preferably configured as bipolar instrument and as such comprises an electrode 17 as well as a neutral electrode 18. However, also other instruments can be used that contain only the electrode 19, but not the neutral electrode 18. In such a case, the neutral electrode is arranged at another location in the instrument test chamber 12, e.g. in the compartment 13 or in the compartment 14.

The instrument 16 is connected with a generator 20 via a cable 19 that can contain, e.g. two conductors connected with the electrode 17 and the neutral electrode 18, wherein the generator 20 can supply an electrical radio frequency voltage to the instrument 16. Preferably the generator 20 is configured to supply different radio frequency voltage forms that are also possible during use on a patient and the physiological effect of which shall be compared in view of neuromuscular stimulations.

A signal differential amplifier 21 is also part of the NMS-test bench 10 according to FIG. 1 that comprises a number of inputs that are connected with diverting electrodes 22, 23, 24, 25 that are arranged in the compartment 13 at the side of the wall 15 that faces away from the instrument 16. The diverting electrodes 22, 23, 24, 25 are preferably arranged along a path or in the proximity of a path along which the obturator nerve extends in a mammal or human being. In addition, the signal differential amplifier 21 can be connected with a reference electrode 26 that is arranged in some distance, preferably at the side of the compartment 13 away from the wall 15. The signal differential amplifier 21 can be connected to a storage device 27, e.g. in form of a storage oscilloscope in order to record and if desired also to display electrical signals diverted from the electrodes 22-25. In case of an activation of the instrument 16, i.e. application of a current to the electrode 17, the voltages that occur at the electrodes 22-25 are detected and recorded.

A switch 28 can be part of the NMS-test bench according to FIG. 1 that is connected with generator 20 as well as the storage 27 in order to activate the instrument 16 in case of actuation and concurrently initiate the recording of the potentials occurring at the electrodes 22-25. In addition, a non-illustrated device can be provided in order to position the instrument 16 in a predefined manner, i.e. to keep it immovably at a specific position in the compartment 14. In a further embodiment the device can also be configured to move the instrument along a predefined path, e.g. toward the wall 15 and away therefrom or along the wall 15. The positioning and movement of the instrument 16 can also be controlled by switch 28. The storage 27 comprises an output 29 at which the signals obtained from the electrodes 22-25 and amplified by the signal differential amplifier 21, stored in the storage 27 are provided or can be provided for transfer to other parts of the test bench.

The part of the NMS-test bench 10 according to FIG. 1 described thus far operates as follows:

For reproducibly detecting electrical voltages that can occur during use of the instrument 16 on tissue of a human or animal body, one or more experiments are carried out with the NMS-test bench 10. For this first an instrument 16 to be tested as well as a desired mode, i.e. a desired RF-voltage form, are selected at the generator 20. In addition to the voltage form, the RF-power and/or the RF-voltage and if necessary other electrical parameters can be defined such as, e.g. maximum current, maximum power, the pulse-pause-ratio of the RF-voltage or a range therefore. In addition, a position of the instrument 16 can be defined in which the instrument 16 is maintained during the experiment. Alternatively, a path can be defined along which the instrument 16 shall be moved during the experiment.

For carrying out the experiment the switch 28 is actuated, which results in applying a current to instrument 16 and for example moving the instrument 16 along the wall 15 over a predefined distance. The voltages occurring thereby at the electrodes 22, 23, 24, 25 are detected, amplified (or attenuated) by the signal differential amplifier 21 and stored in storage 27. The storage 27 can be configured to store a larger number of signals that stem from a larger number of activations, i.e. actuations of the switch 28.

At least one of the signals S gained in this way is now evaluated in the second part 11 of the NMS-test bench in a reproducible manner with regard to its physiological effect. For this the NMS-test bench 11 according to FIG. 2 comprises a nerve model 30 that can be, for example, formed by an electrical network. The nerve model comprises in each case an input 31 and an output 32 that supplies a compound action potential (CAP) 32 or multiple CAPs, if a stimulation signal above a control threshold is supplied to the input 31. In the present case the nerve model 30 is formed by a nerve test chamber 33 that comprises a series of preferably stick-like electrodes orientated parallel to each other in a predefined distance of, e.g. 5 mm, on which a prepared nerve 34 that is, for example removed from an animal, is led such that it contacts the stick-like electrodes.

The part of the NMS-test bench 11 shown in FIG. 2 comprises an input 35 that can be connected with the output 29 of the NMS-test bench 10 according to FIG. 1. The connection can be any connection suitable for data transmission including a radio connection, a light path, a cable connection or a connection via data media, such as CD or stick or via a network. A processing device 36 can be connected to the input 35 that can, e.g. serve for signal filtering. For example, all of the frequency components above a frequency limit of, for example 100 kHz, can be filtered from the signal stored in the storage 27 and thus removed. Alternatively, this part of the signal processing can also be carried out by the signal differential amplifier 21 and/or the storage device 27.

The input 35 is directly connected with a signal generator 37 or indirectly via the signal processing device 36, wherein the signal generator 37 is directly connected with stimulation electrodes 39, 40 of the nerve test chamber 33 or via a signal amplifier 38. The nerve 34 led thereon receives the signal applied to the stimulation electrodes 39, 40.

An amplifier 43 is connected to two other electrodes configured as diverting electrodes 41, 42, the output signal of which is supplied to an oscilloscope, a database or a storage block 44.

It is indicated that single, multiple or all elements of the NMS-test bench 11 illustrated in FIG. 2 can be provided as electrical analog circuit, as digital circuit or as computer model.

For evaluating of the physiological effects of at least one signal determined by the NMS-test bench part 10 of FIG. 1, in the simplest case a mostly disturbance-free signal is selected from the recorded signal. Signals recorded too close to the electrode 17 can be disturbed. Signals recorded too far away can be too weak. Preferably the signal of the electrodes 22-25 is selected that is about 3 mm distant from the cut, i.e. from the electrode 17. In this distance thermal damages of tissue hardly occur, however, neuromuscular stimulations can still be expected.

The selected signal is supplied to the nerve model 30 of the NMS-test bench part 11. For this the signal received at the input 35 is transferred by the signal processing device 36, e.g. low pass filtered, amplified by the signal amplifier 38, if appropriate, and supplied to the stimulation electrodes 39, 40. The prepared nerve 34 reacts to this stimulation by generating of more or less CAPs that can be measured by the diverting electrodes 41, 42 and finally recorded in the storage block 44. Thus, the physiological effects of different signals provided at the input 35 can be evaluated and compared in a reproducible manner.

The reference stimulation signal applied to the electrodes 39, 40 is adjusted in its amplitude, such that the compound action potential 32 delivered by the nerve 34 and received at the diverting electrodes 41, 42 corresponds to a fraction of the maximum CAP. This fraction $CAP_{80}$ is preferably 80% of the maximum CAP.

Also the signals of multiple or all of the electrodes 22-25 can be supplied subsequently to the nerve model 30 in order to find out in this manner in which distance from the cut neuromuscular stimulations still occur and in which distance safe cutting is still possible.

The signal received at the diverting electrodes 41, 42 can be a mixed signal that contains CAPs transmitted from the nerve 34 as well as signal portions created by direct electrical conduction. It is therefore useful to replace nerve 34 by a non-functional nerve that contains a bruise location between the stimulation electrodes 39, 40 and the diverting electrodes 41, 42 at which the stimulation propagation is interrupted. The signal transmitted by such a non-functional nerve to the diverting electrodes 41, 42 can be subtracted from the corresponding signal of the functional nerve 34 measured at the diverting electrodes 41, 42. In doing so, the signal conducted by nerve 34 can be detected and stored free of artifacts, stimulus artifacts are avoided.

Another part of the inventive method refers to the selection of the diverting electrodes 41, 42 from the group of present electrodes. For this a defined standard signal is applied to the stimulation electrodes 39, 40, e.g. a 100 µs square wave pulse of such a voltage that leads with reliability to a complete stimulation of nerve 34, i.e. of all of the contained nerve fibers, such that it supplies the maximum compound action potential CAP. The stimulation signal that is reliably sufficient for this is, e.g. a 7 V signal. Those electrodes are now selected as diverting electrodes 41, 42 that have a predefined distance of, for example 1.5 cm to the stimulation electrodes 39, 40. If the compound action potentials arriving at the diverting electrodes should be too small, i.e. falling below a predefined limit (amplitude), the distance can be shortened, e.g. to 1 cm.

Alternatively, those electrodes 41, 42 can be selected as diverting electrodes 41, 42 at which at least a compound action potential of 3 mV can be measured. If the test is started with the electrode pair that is arranged farthest to the right, diverting electrode pairs are selected that are arranged further to the left, if a compound action potential of at least 3 mV is not achieved. In the next step standard square wave impulses of, for example 100 μs duration can be applied at the stimulation electrodes 39, 40, wherein the stimulation amplitude starts at a low level of, e.g. 100 mV and is increased or decreased in a stepwise manner. If the amplitude that is necessary at the stimulation electrodes 39, 40 in order to be able to detect any compound action potential at the diverting electrodes 41, 42, is larger than 500 mV, electrodes that are arranged farther to the left are selected as diverting electrodes in a stepwise manner. In doing so, those electrodes are selected as diverting electrodes 41, 42 with which a standardized measurement is possible.

According to the invention, a two-part NMS-test bench 10, 11 is provided with which instruments 16, generator voltages and/or surgery modes can be evaluated systematically with regard to neuromuscular stimulations. By separating the NMS-test bench in a first part 10 for application of the instrument and in the second part 11 for evaluation of the physiological effect on nerves 34, a measurement free of artifacts is possible. The spatial and timely separation of the RF application from the recording of the compound action potentials makes RF-disturbances ineffective that otherwise emit from the instrument and disturb the measurement. In addition, the electrical signals gained in the instrument test chamber can be subject to a pre-processing, such as for example a filtering, an amplification or attenuation. The recorded electrical signals emitted from the instrument can be subject to an evaluation at the nerve model 30 in an arbitrary number of times. The variance that is involved with the recording of the compound action potentials during direct use of the instrument can thus be minimized. In addition, the separated test of the obtained signals at the nerve model 30 avoids thermal damage of a prepared nerve 34 and thus a falsification of measurement results. In addition, the equipment expenses for evaluation of electrosurgical systems with regard to neuromuscular stimulations is reduced by the present invention.

LIST OF REFERENCE SIGNS

10 NMS test bench—first part
11 NMS test bench—second part
12 instrument test chamber
13, 14 compartments
15 wall
16 instrument
17 electrode
18 neutral electrode
19 cable
20 generator
21 signal differential amplifier
22-25 electrodes
26 reference electrode
27 storage
28 switch
29 output
30 nerve model
31 input (nerve test chamber)
32 output
33 nerve test chamber
34 nerve
35 input (nerve model)
36 signal processing device
37 signal generator
38 signal amplifier
39, 40 stimulation electrodes
41, 42 diverting electrodes
43 amplifier
44 memory block

The invention claimed is:

1. A method for quantifying neuromuscular stimulations external from a living organism, the method comprising the following steps:
    applying a radio frequency voltage to an instrument (16) located in an instrument test chamber (12) and positioning the instrument in a defined manner,
    recording an electrical signal (S) in the instrument test chamber (12) via at least one electrode (22),
    determining a stimulation signal (A) from the recorded electrical signal (S), and
    stimulating a nerve model (30) with the stimulation signal and detecting compound action potentials (CAPs) output from the nerve model (30).

2. The method according to claim 1, further comprising placing a section of a prepared nerve (34) for use as the nerve model (30) in a nerve test chamber (33) comprising at least one stimulation electrode pair (39, 40) and at least one diverting electrode pair (41, 42), such that the prepared nerve (34) contacts the at least one stimulation electrode pair (39, 40) as well as the at least one diverting electrode pair (41, 42), and applying the stimulation signal (A) to the stimulation electrode (39, 40) and detecting a signal arriving at the diverting electrodes (41, 42) as compound action potentials (CAPs).

3. The method according to claim 1, further comprising storing the recorded electrical signal (S).

4. The method according to claim 1, further comprising processing the recorded electrical signal (S) for determination of the stimulation signal (A).

5. The method according to claim 4, further comprising low pass filtering the recorded electrical signal (S) for determination of the stimulation signal (A).

6. The method according to claim 1, further comprising buffering the stimulation signal (A).

7. The method according to claim 6, further comprising standardizing the stimulation signal (A) by referencing it with a reference stimulation voltage.

8. The method according to claim 7, wherein standardizing the stimulation signal includes applying a reference stimulation signal to the stimulation electrode (39, 40) and determining first the compound action potential (CAP) and subsequently increasing or decreasing the reference stimulation signal until the resulting compound action potential (CAP) is within predetermined limits.

9. The method according to claim 8, further comprising amplifying or attenuating the stimulation signal (A) with an amplification factor determined by a quotient of an amplitude of a stimulation signal providing a predefined fraction ($CAP_{80}$) of the compound action potential (CAP) and an initial amplitude of the reference stimulation signal.

10. The method according to claim 1, further comprising determining a stimulus artifact (ART) by applying the stimulation signal (A) to a non-functional nerve inserted in the nerve test chamber (33).

11. The method according to claim 10, further comprising determining a difference signal by subtracting the stimulus artifact (ART) of the non-functional nerve from the compound action potentials (CAPs) of a functional nerve and evaluating at least one of the instrument (16), the radio frequency voltage, and the positioning of the instrument (16) in view of a potential for neuromuscular stimulations based on the difference signal.

12. A device for quantification of neuromuscular stimulations external from a living organism, the device comprising:
an instrument test chamber (12) that comprises a first compartment (13), a second compartment (14), and a wall (15) separating the first and second compartments, wherein each of the first and second compartments are configured to be at least partly filled with a liquid,
diverting electrodes (22, 23, 24, 25) positioned in the first compartment (13); and wherein the second compartment (14) is configured to receive a device to be tested,
a pre-processing unit (36) to which signals (S) output from the diverting electrodes (22, 23, 24, 25) are supplied, wherein a signal generator (37) is connected to the pre-processing unit (36), and a nerve test chamber (33) configured to receive a prepared nerve (34), wherein the signal generator (37) is connected to the nerve test chamber (33).

13. The device according to claim 12, wherein the wall (15) is a current conducting membrane made of prepared biological material.

14. The device according to claim 12, wherein the nerve test chamber (33) comprises two stimulation electrodes (39, 40) and at least two diverting electrodes (41, 42).

15. The device according to claim 14, wherein the at least two diverting electrodes (41, 42) are configured as sticks arranged in a common plane parallel to each other.

\* \* \* \* \*